United States Patent [19]

Schumacher et al.

[11] Patent Number: 5,109,128
[45] Date of Patent: Apr. 28, 1992

[54] CONTINUOUS CATALYTIC OXIDATION OF ALDITOLS TO ALDOSES

[75] Inventors: Elaine F. Schumacher, Arlington Heights; Blaise J. Arena, Des Plaines, both of Ill.

[73] Assignee: UOP, Des Plaines, Ill.

[21] Appl. No.: 642,766

[22] Filed: Jan. 18, 1991

Related U.S. Application Data

[63] Continuation-in-part of Ser. No. 416,075, Oct. 2, 1989, abandoned.

[51] Int. Cl.$^5$ ............................................. C07H 1/00
[52] U.S. Cl. ..................................... 536/124; 536/1.1; 536/4.1
[58] Field of Search ................... 536/124, 1.1, 4.1

[56] References Cited

PUBLICATIONS

Glattfeld and Gershon, J. Am. Chem. Soc., 60, 2013 (1938).
K. Heyns and H. Paulsen, Ang. Chem., 69, 600 (1957).
K. Heyns and M. Beck, Chem. Ber., 91, 1720 (1958).

Primary Examiner—Johnnie R. Brown
Assistant Examiner—Everett White
Attorney, Agent, or Firm—Thomas K. McBride; Eugene I. Snyder

[57] ABSTRACT

A process is presented for the continuous oxidation of alditols to aldoses accompanied by under 20 weight percent of aldonic and/or alduronic acids relative to the aldoses that are formed. The use of zerovalent platinum on a support such as theta-alumina and at superatmospheric oxygen partial pressures up to about 1,000 pounds per square inch is partially successful in affording good conversion of alditols with relatively low aldonic and/or alduronic acid formation.

26 Claims, 1 Drawing Sheet

CONTINUOUS CATALYTIC OXIDATION OF ALDITOLS TO ALDOSES

CROSS REFERENCE TO RELATED APPLICATION

This application is a continuation-in-part of my copending application, Ser. No. 416,075, filed Oct. 2, 1989, now abandoned, all of which is hereby incorporated by reference.

BACKGROUND OF THE INVENTION

A general method of gaining entry into the rare aldoses has been sought for over 50 years with little apparent success but with little diminution in the desirability of or motivation for finding and developing appropriate chemical procedures. One approach which has been explored with mixed success is the oxidation of alditols to the corresponding aldoses of the same carbon number. By "alditol" is meant a polyhydroxylic compound of general formula $HOCH_2(CHOH)_nCH_2OH$, sometimes referred to as a sugar alcohol. Of this class the tetritols (n=2), pentitols (n=3), and hexitols (n=4) are the most important representatives. The corresponding aldoses have the formula $HOCH_2(CHOH)_n$-CHO, where n=2 corresponds to the tetroses, n=3 to the pentoses, and n=4 to the hexoses. Glattfeld and Gershon made several pertinent observations in their investigation of the oxidation of mannitol and galactitol (dulcitol) [*J. Am Chem. Soc.,* 60, 2013 (1938)]. From a preliminary study of the oxidation of mannose they concluded that the operative reaction sequence was

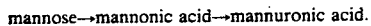

Using platinum oxide to oxidize mannitol they observed that platinum oxide was reduced to zerovalent platinum accompanied by the stoichiometric oxidation of mannitol. The zerovalent platinum then catalyzed the oxidation of mannitol by oxygen. The oxidation of mannitol afford major amounts of carboxylic acids (more than about ⅓ of the product) and the investigators proposed a squence

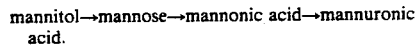

Generalizing from the above one may then write the sequence,

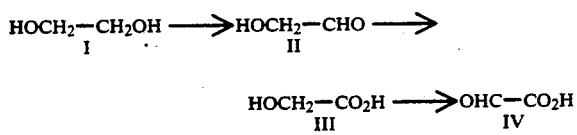

from which one can draw several conclusions. The conversion of II (aldose) to III (aldonic acid) implies that under the reaction conditions the aldehydric functional group, CHO, is oxidized faster than is the primary hydroxyl group, $CH_2OH$. The fact that both II and II+IV are present in the reaction mixture implies that the oxidation of $CH_2OH$ is at least competitive with that of CHO, for if CHO were oxidized much faster than $CH_2OH$ then at least II and perhaps IV also should be minor products, contrary to what was observed.

Somewhat later K. Heyns and H. Paulsen, *Ang. Chem.* 69, 600 (1957) used zerovalent platinum supported on charcoal as a catalyst in the oxidation of alditols by oxygen. These workers proceeded on the basis that in the oxidation the rate determining step was dehydrogenation, and oxygen merely served as an acceptor for "activated hydrogen" to remove the latter from equilibrium through formation of water. This seemed to be confirmed by their report that the use of higher oxygen pressure offered no advantage. They also reported that primary alcohol groups are generally oxidized in neutral to slightly acidic solution as far as the aldehyde stage and only to a very slight degree further to the acid. However, aldehyde yields were not always satisfactory. These same workers also stated that the aldehyde group of aldoses can be readily oxidized to their carboxylic acids.

Almost contemporaneously K. Heyns and M. Beck, *Chem. Ber.*, 91, 1720 (1958) described the preparation of L-gulose by the oxidation of sorbitol using zerovalent platinum supported on carbon. They noted that the medium had a profound effect on the course of oxidation, consistent with their prior observation that oxidation of erythritol in glacial acetic acid afforded only reducing reaction products with no acid formation, and with decreasing acetic acid content in aqueous systems the yields of reducing substances and byproducts increased. Similarly, in the oxidation of sorbitol the aldose yields increased significantly upon changing from 30% acetic acid to water as a reaction medium. However, the ratio of uronic acid to aldose also increased, going from a low of 0.07 in 30% acetic acid to 1.53 in water at 60° C. After 8 hours, oxidation in water at 40° C. afforded a total yield of only 35-8% aldoses and 10-12% uronic acids. The aldoses were shown to be D-glucose and L-gulose when D-sorbitol was the alditol. There was also an implication that the zerovalent platinum on carbon was readily poisoned.

It seems that the aforementioned teachings particularly pertinent to the present application may be fairly summarized as follows. 1. Oxidation of alditols in water at autogeneous pH as catalyzed by zerovalent platinum and effected by oxygen, affords aldoses in yields under 40% accompanied by major amounts of carboxylic acids as coproducts, with the weight ratio of acids to aldoses being generally greater than about 0.3, presumably because the oxidation of the aldehyde functionality is easier than, or competitive with, the oxidation of the hydroxymethyl group when catalyzed by zerovalent platinum. 2. These oxidations are unaffected by oxygen pressure because oxygen is not involved in the rate determining step. 3. There is some indication that zerovalent platinum has a limited lifetime as a catalyst in these oxidations, which is consistent with our observations in other unrelated work that, for example, gluconic acid and/or glucuronic acid serves as a potent poison to zerovalent platinum catalysts.

In contrast to the prior art, we have developed a method of oxidizing alditols using as a catalyst zerovalent platinum on selected supports and using oxygen at superatomspheric pressure. Our method affords aldoses in a product mixture containing less than about 20 weight percent carboxylic acids relative to the formed aldoses. To put this into perspective, in our method the acid: aldose product ratio is less than 0.2, whereas the comparable ratio found in the prior art methods seems to be at least 0.3. Furthermore, the relatively low acid-:aldose product ratio is maintained even with aldose yields of 50% and better. Because our catalyst is not readily poisoned under reaction conditions, perhaps because of our relatively low acid yields, the oxidation can be effected in a continuous process. Thus our invention has the advantages of being more selective, especially with respect to carboxylic acid formation, of effecting relatively high conversion of alditol in a reasonable time, and of being capable of being performed in a continuous process, thereby making it significantly advantageously over the prior art. n comparison to the work of Heyns and Beck, we have achieved higher selectivity and higher aldose yields by effecting oxidation at superatomspheric pressure, whereas the achieved higher selectivity at a sacrifice in aldose yields by using acetic acid in the reaction medium.

SUMMARY OF THE INVENTION

The purpose of our invention is to selectively oxidize alditols, especially in a continuous manner, to aldoses with the formation of less than 20 weight percent aldonic and alduronic acids relative to the formed aldoses. An embodiment comprises flowing an aqueous solution of the alditol over a fixed mass of a supported zerovalent metal which is platinum, palladium, rhodium, or ruthenium in the presence of oxygen at a partial pressure of more than about 20 pounds per square inch, and up to at least 1,000 pounds per square inch. In a more specific embodiment the catalyst is platinum. In a still more specific embodiment the catalyst is platinum deposited on theta-alumina. In a yet more specific embodiment the oxidation is effected at a pressure between about 35 and about 200 pounds per square inch of oxygen. Further embodiments will become apparent from the ensuing description.

DESCRIPTION OF THE INVENTION

Figure 1:
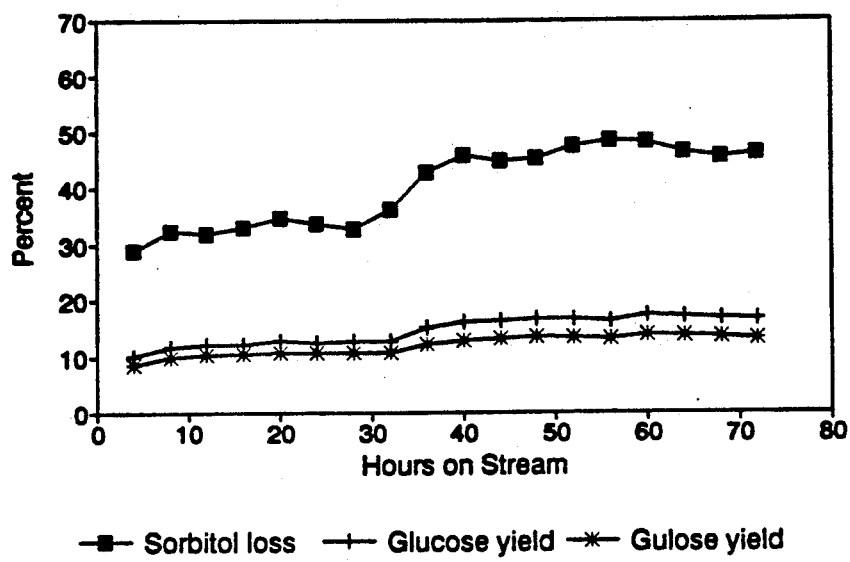
FIG. 1 is a graphical representation of sorbitol oxidation at 1000 psig air using a fixed bed of 5 weight percent platinum on theta-alumina with a feedstock flow of 1 LHSV. The temperature was 80° for the first 32 hours, and 90° C. thereafter.

We have found that if alditols are oxidized using a bed of certain zerovalent metals on selected supports, especially in a continuous reaction, and especially at an elevated oxygen pressure, one can obtain reasonable conversion of the alditol (I) to one or more aldoses (II) while maintaining aldonic and/or alduronic acid levels at less than about 20 weight percent relative to aldose. By "aldonic acid" is meant an acid corresponding to III; by "alduronic acid" is meant an acid corresponding to IV. Since the alditol often can be formed by reduction of a common aldose, and since oxidation of the alditol often affords as one of its products a rare or unusual aldose, our method forms an important link in obtaining rare aldoses from common raw materials.

The reactant or feedstock in the process which is our invention is an aqueous solution of an alditol which is generally, but not necessarily, at autogeneous pH. High concentrations of alditols in the feed are preferred for maximizing productivity. There is, at least in principle, no upper concentration limit so long as the feedstock remains homogeneous and is not so viscous as to cause problems in pumping and so forth. Normally feedstocks contain between 10 and about 30 weight percent alditols, although as suggested above these are concentrations chosen solely for convenience and form no limitation on our invention. The alditols which may be used as a reactant include tetritols, pentitols, and hexitols, and of these the tertritols are the least likely to be used. Examples of alditols which may be used in the practice of our invention include arabitol, ribitol, xylitol, sorbitol, mannitol, galactitol, talitol, and iditol.

As was noted previously, decreasing the pH of the oxidation medium as effected by adding acetic acid suppresses aldose formation, but suppresses acid formation even more strongly. Thus, even though our method affords superior results at autogeneous pH it may well be that another, quite particularized result may be attained by judicious adjustment of the pH. What we wish to emphasize, however, is that the success of our method per se is not dependent upon the pH of the reaction medium.

The aqueous solution of alditol is then contacted with a mass of certain zerovalent metals composited on selected supports. The zerovalent metals which can be use in any combination in our invention include platinum and palladium and, to a lesser extent, rhodium and ruthenium, and of these platinum is most preferred. The supports which may be used in the composites include polymeric organic resins, theta-alumina, carbon, and titania. Among the preferred resins are polystyrenes, poly(vinylpyridine), and polyacrylamides. It is preferred that the polymeric organic resins have a surface area of at least $30m^2/g$. Resins having a surface area greater than about 50 $m^2/g$ are preferred, and those with a surface area over about 100 $m^2/g$ are even more highly preferred.

There is nothing unusual or exceptional in the preparation of these catalysts. Normally the support is impregnated with a suitable soluble compound of the metal, and subsequent reduction of the impregnated metal salt in a hydrogen atmosphere affords the zerovalent metal dispersed on the support. Methods of compositing zerovalent metals on supports are well known to those in the art and will not be further elaborated upon. Generally the catalyst contains less than about 10 weight percent of the zerovalent metal. The major effect of the zerovalent metal concentration on the catalyst is on the rate of oxidation, and it has been found that catalysts containing between about 1 and about 5 weight percent of the zerovalent metal are the best compromise. At higher concentrations the dispersion of the metal becomes lower (i.e., the metal tends to agglomerate in larger particles) leading to less efficient utilization of the metal, and at lower concentrations the reaction rate is undesirably low.

The alditol may be oxidized using oxygen at ambient pressure. Since air is at a pressure of about 14.5 pounds per square inch and contains 20% oxygen, ambient oxygen pressure corresponds to a partial pressure of oxygen of about 3 pounds per square inch. However, our invention is based on the finding of significant advantages attending oxidations conducted at superatmospheric oxygen pressures and the success of our invention is significantly increased by using increased oxygen pressures, up to about 1,000 pounds per square inch. Higher partial pressures of oxygen also may be used in the practice of our invention, but not necessarily with any benefit. Generally, oxygen will be used at a partial pressure of at least 20 pounds per square inch and more usually at a partial pressure of at least 35 pounds per square inch. The oxygen partial pressure in the most usual cases is up to about 200 pounds per square inch. Partial pressures of oxygen between about 35 and about 200 pounds per square inch normally are used in the practice of our invention. The use of elevated pressures is a major distinction of our process over the prior art with the major effect of increased oxygen partial pressures being an increased conversion of the alditol to the desired product aldose in any given time interval. It also may be that increasing oxygen partial pressure has more of an effect on the rate of oxidation of the hydroxymethyl group to the aldehyde functionality than it does on the rate of oxidation of the aldehyde group to a carboxylic acid functionality, with this differential rate effect resulting in an increased amount of aldose formed relative to that of the carboxylic acid. It also needs to be emphasized that the greatest selectivity (in the sense of carboxylic acid/aldose ratio) in alditol oxidation results from a judicious choice of reaction temperature and oxygen partial pressure.

The oxidation generally is run at a temperature under 95° C., since many of the aldoses are thermally unstable at a temperature above 95° C. The minimum temperature is operationally defined as that where the alditol conversion rate is acceptable even at the highest partial pressure of oxygen contemplated in the practice of this invention, i.e., 1,000 pounds per square inch of oxygen. Reaction temperatures below about 20° C. are not favored, and generally a reaction temperature between about 40° and about 90° C. is most preferred.

Although the oxidation of alditols using the catalysts of our invention may be performed in a batch reaction, the oxidation has greatest utility when performed in a continuous manner. When the reaction is run continuously one can utilize a fixed bed, an ebullating bed, a fluidized bed, and so forth, with a fixed bed preferred largely because it provides the simplest way of carrying out the reaction. The aqueous feedstock of alditol may be used either as an upflow or a downflow stream, although the downflow mode of operation is more conventional. The oxygen stream may be either concurrent or countercurrent to the aqueous alditol stream. When the oxygen is fed countercurrently there is better mixing, and for this reason a countercurrent flow of oxygen is preferred.

Using a fixed bed as an example, an aqueous stream of alditol may be passed downflow over a fixed mass of a supported zerovalent metal. The most preferred catalyst is a zerovalent platinum deposited on theta-alumina or on a polystyrene having a surface area greater than about 30 m$^2$/g. Oxygen will be passed through the flowing stream and through the catalyst bed countercurrently at a pressure between about 20 and about 1,000 psi of oxygen, but most desirably between about 35 and about 200 psi oxygen. The reaction zone will be maintained at a temperature no greater than 95° C. and normally will be in the range from about 40 to about 90° C. The liquid hourly space velocity of the alditol normally will be in the range from about 0.1 to about 5.0. Effluent is collected and will contain under about 20 weight percent of aldonic and/or alduronic acids relative to the aldose present in the product mixture. Although the acid; aldose ratio is not more than 0.2, a ratio of under 0.15 is preferred, and one under about 0.1 is even more preferred in the practice of our invention. Conversions of alditol generally will be in the neighborhood of 50–60 percent.

The examples which follow merely serve to illustrate our invention and several of its features. These examples are not to be taken as limiting the invention in any way and it needs to be clearly understood that their sole purpose is to exemplify our invention.

EXAMPLE I

Variation of zerovalent metal and support. Batch reductions were performed in a rotating autoclave using as a feedstock an aqueous solution of 9.1 weight percent D-sorbitol. Catalysts were prepared as follows.

A sample of theta-alumina was weighed out to give a desired volume, calculated from the apparent bulk density of the support. An aqueous noble metal chloride solution, of known metal content, was weighted into a graduated cylinder to give an amount of metal equal to 5.0% of the weight of the support used. Concentrated HCl (37.2 wt.% HCl) was then weighed into the graduate, in an amount equal to 2.0 wt.% of the weight of the support. The noble metal/HCl solution was diluted to a volume equal to the volume of the support, using deionized H$_2$O. The solution was then transferred to a steam-jacketed rotary evaporator, and the support was added to it. The mixture was cold rolled for one hour, then evaporated to dryness using steam heat, at atmospheric pressure.

The impregnated support was calcined for two hours in a tube furnace, in an air flow of approximately 7 SCFH at 100°–350° C. After a 15-minute N$_2$ purge. H$_2$ flow was begun at a low rate, and gradually increased to 7 SCFH when there was no longer evidence of an exotherm in the catalyst bed. Flow rate was then maintained for three hours, with a bed temperature of 100°–350° C. The bed was cooled under flowing N$_2$.

Oxidation was performed at 85° C. using catalyst in an amount sufficient to provide 0.014 mmole metal per mmole D-sorbitol and was performed for 24 hours at 140–150 psig (pounds per square inch gage) air or for 16 hours at 1000 psig air, with both sets of results summarized in the following table.

TABLE 1

Effect of Metal or Oxidation

| Catalyst Description | Sorbitol conversion | Selectivity | | |
|---|---|---|---|---|
| | | glucose | gulose | unknowns |
| PtO$_2$ | 69.5 | 48.8 | 42.0 | 9.2 |
| Pd/Carbon | 79.2 | 48.5 | 38.9 | 12.6 |
| Rh/Carbon | 16.8 | 58.3 | 34.5 | 7.2 |
| Ru/Carbon | 9.6 | 30.2 | 29.2 | 40.6 |
| Pt/Θ-Al$_2$O$_3$ | 82.5 | 45.5 | 31.5 | 23.0 |
| Pd/Θ-Al$_2$O$_3$ | 43.7 | 43.2 | 24.3 | 32.5 |
| Ru/Θ-Al$_2$O$_3$ | 27.7 | 30.3 | 25.6 | 44.1 |
| Rh/Θ-Al$_2$O$_3$ | 12.4 | 46.8 | 33.9 | 19.3 |

The foregoing data show that platinum is the most effective metal of those tested.

EXAMPLE II

Effect of pressure. Batch reductions were done using a 5% platinum on theta-alumina catalyst in a rotating autoclave using a feedstock of 9.1 weight percent D-sorbitol at 85° C. Oxidations were performed at 180, 300, and 1120 pounds per square inch (gage pressure) of air. The results of analyses after 16 hours are given in the following table. For comparison, oxidations performed for 8 hours at 85° C. and 1,000 psig air also were performed using as catalyst unsupported platinum oxide (which is converted to colloidal platinum under reaction conditions) and 5% platinum on theta-alumina.

TABLE 2

Effect of Pressure on D-Sorbitol Oxidation[a]

| Pressure psig[b] | Sorbitol conversion | Selectivity | | |
|---|---|---|---|---|
| | | glucose | gulose | unknowns |
| 180 | 61 | 50 | 38 | 13 |
| 300 | 68 | 50 | 38 | 12 |
| 1120 | 83 | 46 | 32 | 23 |
| 1000[c] | 6 | 47 | 37 | 16 |
| 1000 | 73 | 45 | 34 | 21 |

[a]0.014 mmole Pt/mmole D-sorbitol unless otherwise noted.
[b]Air pressure.
[c]Catalyst is unsupported $PtO_2$.

EXAMPLE III

Effect of Temperature of Oxidation. Batch reductions were performed as previously described using the aforementioned feedstock of d-sorbitol and catalyst in an amount sufficient to provide 0.014 millimode platinum per millimole D-sorbitol at a pressure of either 50 or 1,000 pounds per square inch (gage) of air. Results are summarized in the following Table 3.

TABLE 3

Effect of Temperature on D-Sorbitol Oxidation[a]

| T, °C. | Sorbitol conversion | Selectivity | | |
|---|---|---|---|---|
| | | glucose | gulose | unknowns |
| 40[a] | 1.7 | 17.6 | 17.6 | 64.7 |
| 55[a] | 2.9 | 20.7 | 20.7 | 58.6 |
| 70[a] | 43.9 | 45.1 | 45.1 | 9.8 |
| 80[a] | 53.7 | 48.0 | 39.5 | 12.5 |
| 95[a] | 71.0 | 48.2 | 41.4 | 10.4 |
| 85[b] | 82.5 | 45.5 | 31.5 | 23.0 |
| 95[b] | 87.9 | 45.2 | 24.1 | 30.7 |

[a]Air at 50 psig; 24 hour reaction time.
[b]Air at 1000 psig; 16 hour reaction time.

EXAMPLE IV

Figure 2:
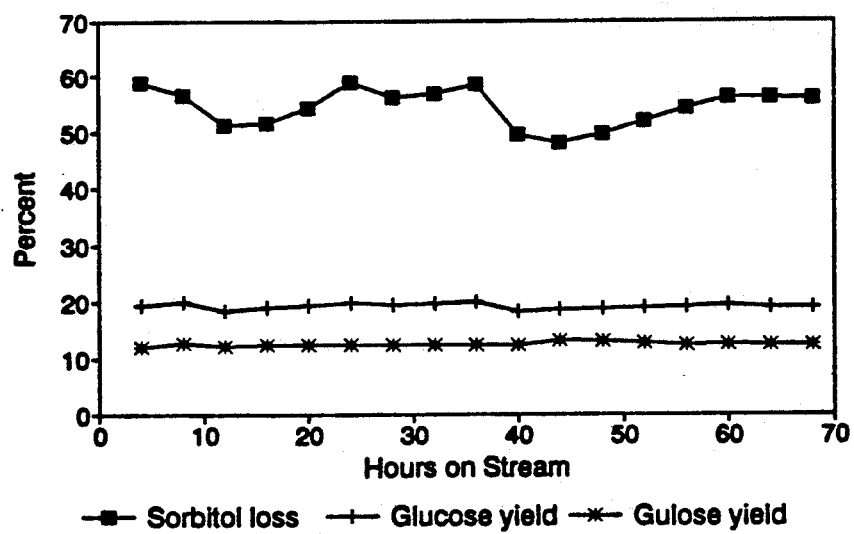
FIG. 2 is a graphical representation of the continuous oxidation of sorbitol at 1000 psig air using a fixed bed of 2.5 weight percent platinum on a high surface area polystyrene at 80° C. with a feedstock flow of 1 LHSV.

Continuous fixed bed sorbitol oxidation. A feedstock of 10.0 weight percent D-sorbitol was passed downflow over a fixed bed of either 5.0 weight percent platinum on theta-alumina or 2.5 weight percent platinum on a high surface area (725 m²/g) polystyrene available from Rohm and Haas as XAD-4. Both oxidations were performed using air at 1,000 pounds per square inch (gage) and at temperatures of 80° or 90° C. In all cases feedstock was passed downflow at 1 LHSV and air was bubbled countercurrent to the feedstock flow. Results are graphically presented in FIGS. 1 and 2. From the two graphs one can see the XAD-4 appears to be the more active catalyst and affords higher conversion with unchanged selectivity. Analysis of the effluent from continuous hydrogenation using theta-alumina as the support showed low leaching of both aluminum and platinum as shown in the following Table.

TABLE 4

Hydrothermal Stability of 5% Platinum on Theta-Alumina

| Time | ppm Aluminum | ppm Platinum |
|---|---|---|
| 12 | 87 | 3.5 |
| 36 | 92 | 3.7 |
| 72 | 80 | 3.1 |

In both of the continuous oxidations product was analyzed by HPLC for gluconic acid, and in both cases less than 0.7 weight percent gluconic acid was present in the product mixture.

EXAMPLE IV

Oxidation of other alditols. A feedstock of 10 weight percent D-arabitol may be oxidized at 85° C. at an air pressure of 300 psig in the presence of 5% Pt supported on polystyrene in an amount sufficient to provide 0.01 mmole metal per mmole arabitol. After 24 hours a 50% conversion of D-arabitol may be obtained with a 95% selectivity to D-arabinose and D-lyxose. Similar results may be obtained with D-talitol using a catalyst of 2% palladium on titania to afford D-altrose, and with D-iditol using a catalyst of 3% Pd on poly(vinylpyridine) to afford D-idose.

What is claimed is:

1. A process of continuous oxidation of an alditol having from 4 to 6 carbon atoms to one or more aldoses of the same carbon number with concurrent formation of less than about 20 weight percent aldonic and alduronic acids relative to the aldoses, comprising flowing a stream of an aqueous solution of the alditol through a fixed mass of a zerovalent metal selected from the group consisting of platinum, palladium, ruthenium, and rhodium, or any combination thereof, composited on a support of theta alumina, titania, carbon, or an organic polymeric resin with a surface area of at least 30 square meters per gram and selected from the group consisting of polystyrenes, polyacrylamides, and poly(vinylpyridines) in the presence of oxygen at a partial pressure of at least 20 and up to about 1,000 pounds per square inch at a temperature from about 20 up to about 95° C.

2. The process of claim 1 where the zerovalent metal is platinum or palladium.

3. The process of claim 2 where the zerovalent metal is platinum.

4. The process of claim 1 where the support is theta-alumina.

5. The process of claim 1 where the surface area is greater than about 50 square meters per gram.

6. The process of claim 5 where the surface area is greater than about 100 square meters per gram.

7. The process of claim 1 where the resin is polystyrene.

8. The process of claim 1 where the zerovalent metal is platinum and the support is theta-alumina.

9. The process of claim 1 where the zerovalent metal is platinum and the support is a polystyrene with a surface area greater than about 100 square meters per gram.

10. The process of claim 1 where the partial pressure of oxygen is at least about 35 pounds per square inch.

11. The process of claim 1 where the partial pressure of oxygen is in the range from about 35 to about 200 pounds pr square inch.

12. The process of claim 1 where the temperature is from about 40 to about 90° C.

13. The of claim 1 further characterized in that the aldoses are formed in at least 50 percent yield.

14. A process of oxidizing an alditol having from 4 to 6 carbon atoms to one or more aldoses of the same carbon number with concurrent formation of less than about 20 weight percent aldonic and alduronic acids relative to the aldoses, comprising reacting an aqueous solution of the alditol with oxygen at a partial pressure of at least 20 and up to about 1,000 pounds per square inch in the presence of a zerovalent metal selected from the group consisting of platinum, palladium, ruthenium, and rhodium, or any combination thereof, composited on a support of theta-alumina, titania, carbon, or an organic polymeric resin with a surface area of at least 30 square meters pre gram and selected from the group consisting of polystyrenes, polyacrylamides, and poly(vinylpyridine) at a temperature from about 20 up to about 95° C.

15. The process of claim 14 where the zerovalent metal is platinum or palladium.

16. The process of claim 15 where the zerovalent metal is platinum.

17. The process of claim 14 where the support is theta-alumina.

18. The process of claim 14 where the polymeric organic resin has a surface area of at least 50 square meters per gram.

19. The process of claim 18 where the surface area is at least 100 square meters per gram.

20. The process of claim 14 where the resin is polystyrene.

21. The process of claim 14 where the zerovalent metal is platinum and the support is theta-alumina.

22. The process of claim 14 where the zerovalent metal is platinum and the support is a polystyrene with a surface area greater than about 100 square meters per gram.

23. The process of claim 14 where the partial pressure of oxygen is at least 35 pounds per square inch.

24. The process of claim 14 where the partial pressure of oxygen is in the range from about 35 to about 200 pounds per square inch.

25. The process of claim 14 where the temperature is from about 40 to about 90° C.

26. The process of claim 14 further characterized in that the aldoses are formed in at least 50 percent yield.

* * * * *